United States Patent
Lin et al.

(10) Patent No.: US 9,915,785 B2
(45) Date of Patent: Mar. 13, 2018

(54) METHODS AND APPARATUS FOR PEDESTAL RING RESONATORS

(71) Applicants: Pao Tai Lin, Brighton, MA (US); Jurgen Michel, Arlington, MA (US); Anuradha Murthy Agarwal, Weston, MA (US)

(72) Inventors: Pao Tai Lin, Brighton, MA (US); Jurgen Michel, Arlington, MA (US); Anuradha Murthy Agarwal, Weston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/591,023

(22) Filed: May 9, 2017

(65) Prior Publication Data

US 2017/0242194 A1   Aug. 24, 2017

Related U.S. Application Data

(63) Continuation of application No. PCT/US2015/062590, filed on Nov. 25, 2015.
(Continued)

(51) Int. Cl.
*G01J 5/02*  (2006.01)
*G02B 6/293*  (2006.01)
(Continued)

(52) U.S. Cl.
CPC ....... *G02B 6/29338* (2013.01); *G01N 21/648* (2013.01); *G01N 21/65* (2013.01);
(Continued)

(58) Field of Classification Search
CPC ... G01N 21/65; G01N 21/648; G01N 21/7746
(Continued)

(56) References Cited

U.S. PATENT DOCUMENTS

| 8,648,306 B1 | 2/2014 | Goertz et al. |
| 2009/0067773 A1* | 3/2009 | Krug .................. G02B 6/12007 385/9 |

(Continued)

OTHER PUBLICATIONS

International Search Report and Written Opinion dated Mar. 11, 2016 from International Application No. PCT/US2015/062590, 10 pages.
(Continued)

*Primary Examiner* — David Porta
*Assistant Examiner* — Meenakshi Sahu
(74) *Attorney, Agent, or Firm* — Cooley LLP

(57) ABSTRACT

A device includes a substrate, a pedestal extending from the substrate, and a ring resonator disposed on the pedestal above the substrate. The ring resonator has a resonance wavelength greater than 1.5 μm and includes at least one of silicon and chalcogenide glass. The device can be used as a ring resonator sensor or a light source. The ring resonator is substantially transparent to mid-infrared radiation to reduce optical losses. The pedestal has a narrower width compared to the ring resonator to generate improved interaction between evanescent fields of light in the ring resonator and analytes nearby the ring resonator, thereby increasing sensing sensitivity. In addition, fabrication of the device is compatible with complementary metal-oxide-semiconductor (CMOS) processes and hence is amenable to large scale manufacturing.

30 Claims, 10 Drawing Sheets

Related U.S. Application Data

(60) Provisional application No. 62/084,643, filed on Nov. 26, 2014.

(51) Int. Cl.
*G02B 6/122* (2006.01)
*G01N 21/64* (2006.01)
*G01N 21/65* (2006.01)
*G01N 21/77* (2006.01)
*G02B 6/12* (2006.01)

(52) U.S. Cl.
CPC ......... *G01N 21/7746* (2013.01); *G02B 6/122* (2013.01); *G02B 6/29395* (2013.01); *G02B 2006/12038* (2013.01); *G02B 2006/12061* (2013.01)

(58) Field of Classification Search
USPC ...................................................... 250/341.1
See application file for complete search history.

(56) References Cited

U.S. PATENT DOCUMENTS

2012/0236895 A1   9/2012  Miles et al.
2014/0264030 A1*  9/2014  Lin ....................... G02B 6/136
                                                      250/338.4

OTHER PUBLICATIONS

International Preliminary Report on Patentability dated Jun. 8, 2017 from International Application No. PCT/US2015/062590, 8 pages.

* cited by examiner

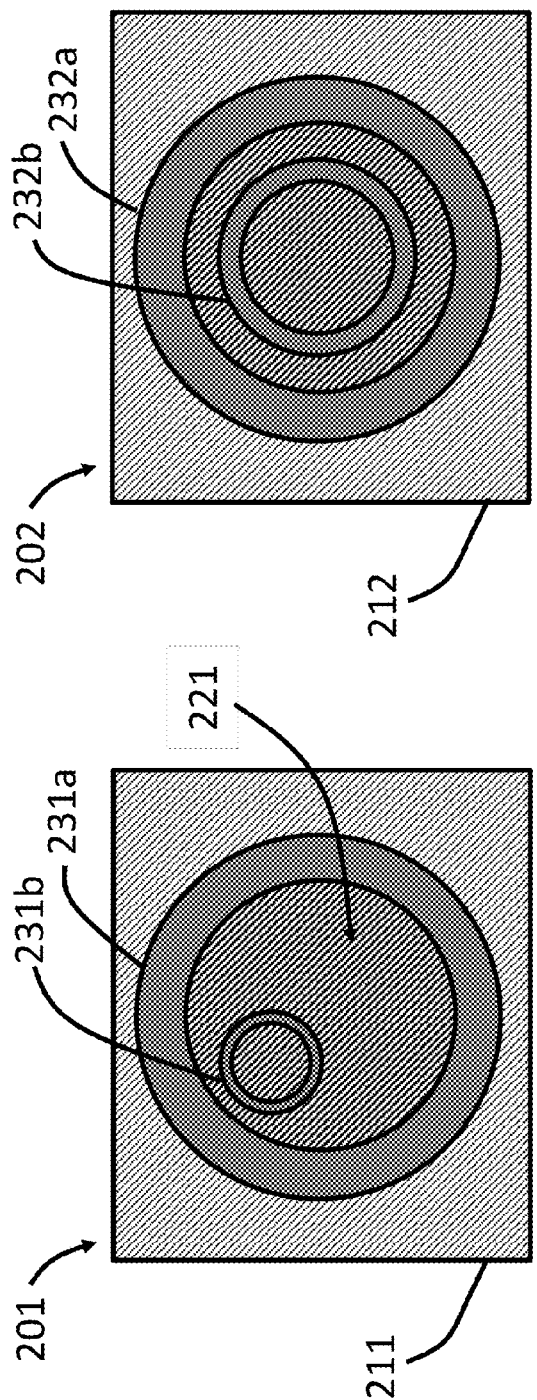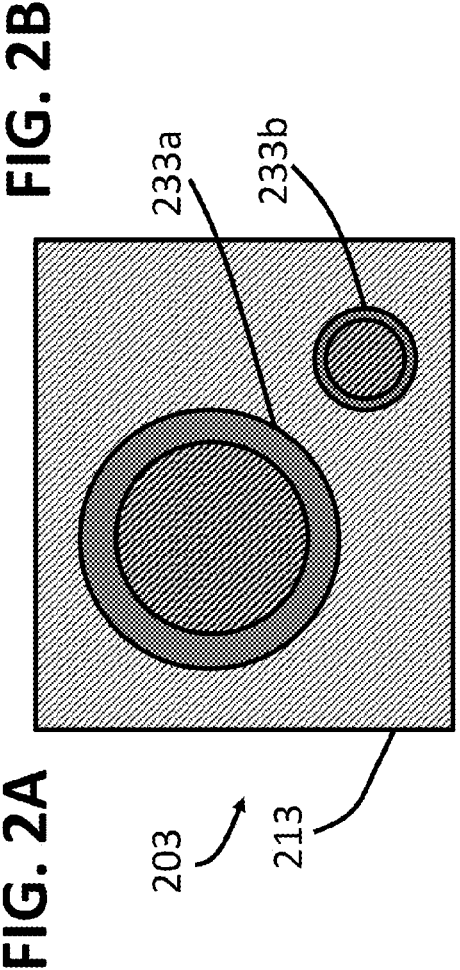
FIG. 2A
FIG. 2B
FIG. 2C

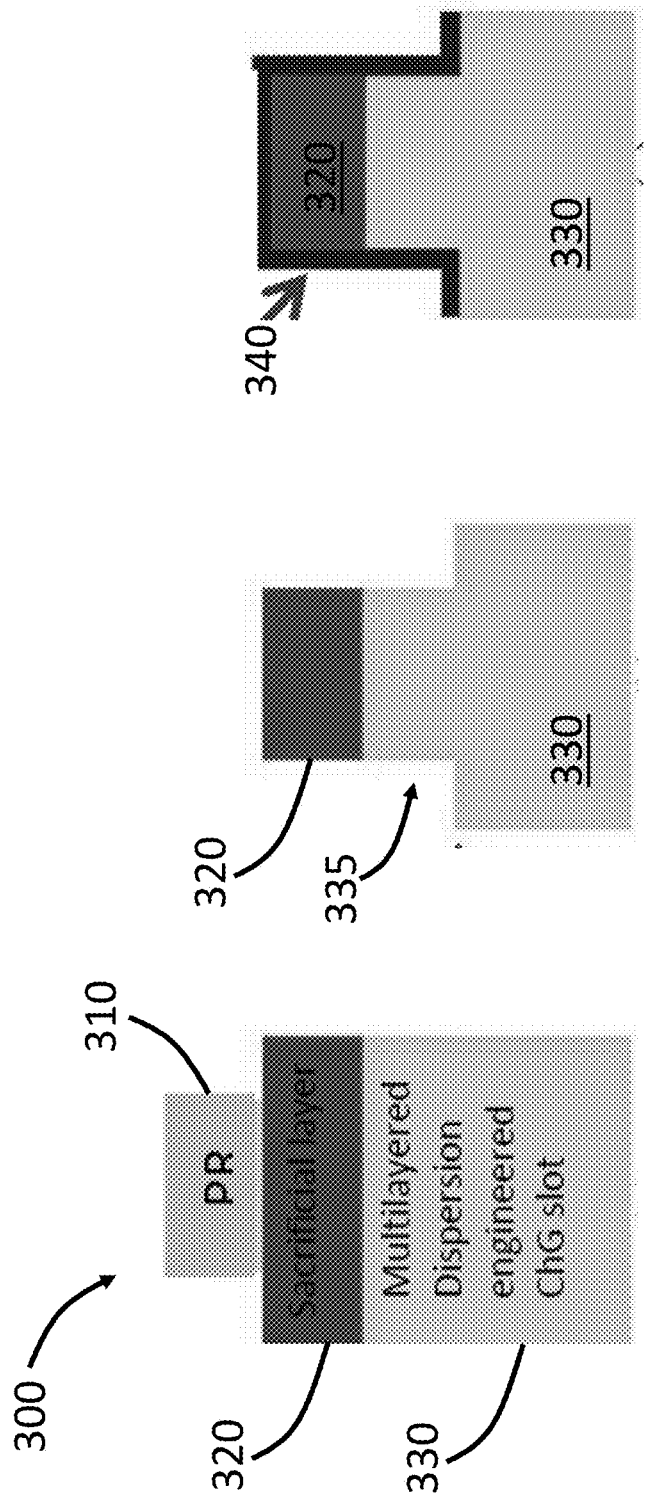

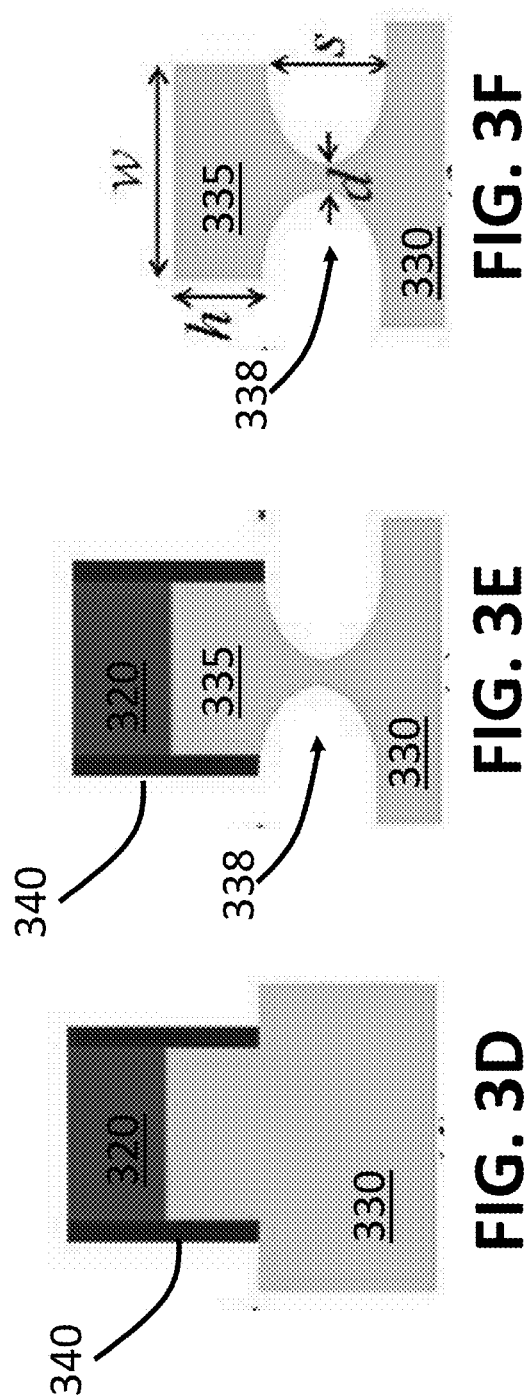

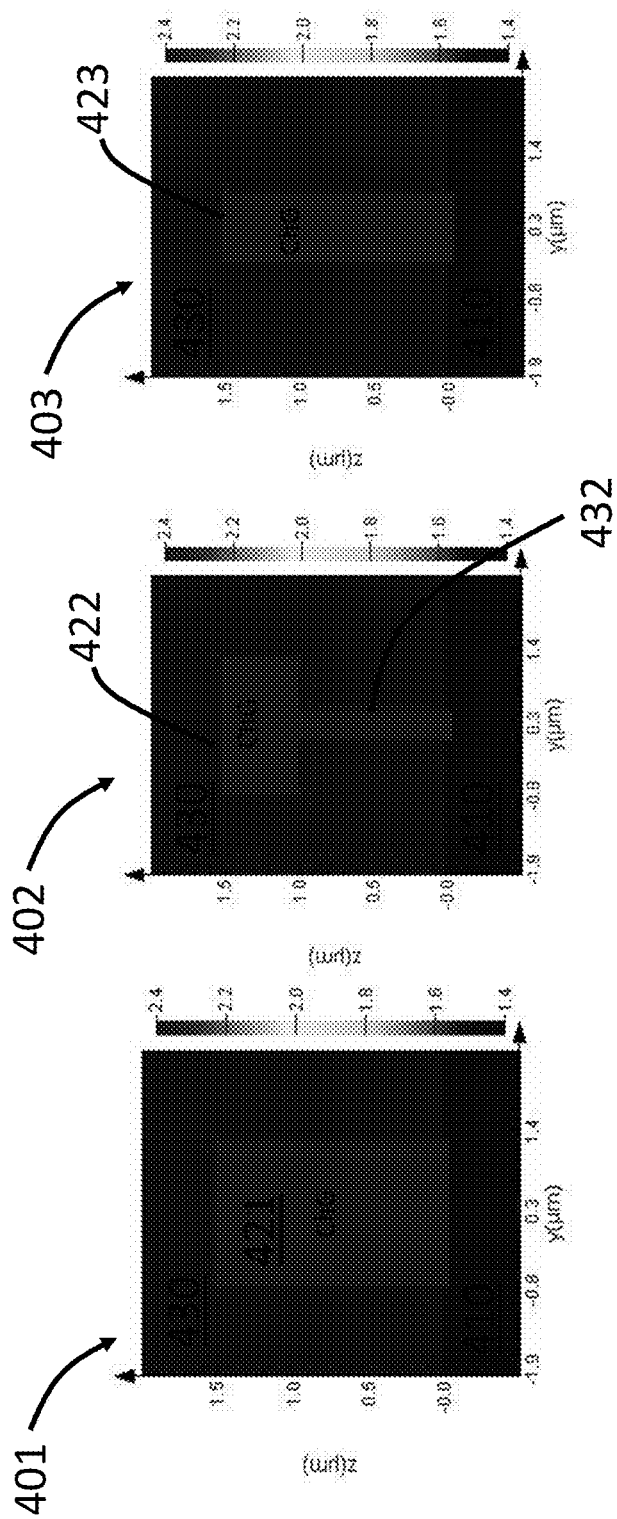

METHODS AND APPARATUS FOR PEDESTAL RING RESONATORS

CROSS-REFERENCES TO RELATED APPLICATIONS

This application is a bypass continuation of International Application No. PCT/US2015/062590, filed Nov. 25, 2015, and entitled "METHODS AND APPARATUS FOR PEDESTAL RING RESONATORS, which in turn claims priority to U.S. Application No. 62/084,643, filed Nov. 26, 2014, entitled "PEDESTAL MICRORING RESONATORS FOR ENHANCED SENSING," each of which is hereby incorporated herein by reference in its entirety.

BACKGROUND

A ring resonator can be regarded as a ring-shaped waveguide. The resonance wavelength $\lambda$ of the mth mode in a ring resonator is $\lambda=2\pi r n_{eff}/m$, where r is the resonator radius, $n_{eff}$ is the effective refractive index (RI) of the mth mode of the ring resonator, and m is an integer. Light propagating in a ring resonator circulates along the ring resonator and has an evanescent field that can reach several hundred nanometers into the surrounding medium (e.g., liquid, gas, and polymer coatings, etc.), which can contain analytes. Therefore, the light propagating through the ring resonator can interact repeatedly with the analytes on or near the surface of the ring resonator.

When used as sensors, ring resonators can have a long interaction length with small physical sizes. For conventional linear waveguide sensors or fiber sensors, the interaction length between light and analytes is essentially the physical length of the waveguide/fiber. In comparison, ring resonator sensors can create an extremely long effective interaction length by circulating the light multiple times in the resonator. The effective interaction length can be expressed as $L_{eff}=Q\lambda/(2\pi n)$, where Q is the quality factor, or Q-factor, of the resonator. Depending on ring resonator configuration, the Q-factor can be about $10^4$ to about $10^8$. Therefore, even with a small physical size (e.g., on the order of microns), the ring resonator sensor can have an effective interaction length of a few tens of centimeters or even longer, resulting in higher sensitivity, smaller footprint, and higher multiplexing capability while using less analyte.

Ring resonator sensors can be used for detecting a variety of chemical and biological species including, but are not limited to, DNA, proteins, viruses, nanoparticles, bacteria, heavy metals, pesticides, and volatile organic compounds (VOCs) in liquid or gaseous phases.

SUMMARY

Embodiments of the present invention include apparatus, systems, and methods of ring resonators supported by pedestals. In one example, a device includes a substrate, a pedestal extending from the substrate, and a ring resonator disposed on the pedestal above the substrate. The ring resonator has a resonance wavelength greater than 1.5 μm and is made of at least one of silicon and chalcogenide glass.

In another example, a method of using a device including a substrate, a pedestal extending from the substrate, and a ring resonator disposed on the pedestal above the substrate is disclosed. The ring resonator is made of at least one of silicon and chalcogenide glass and has a resonance wavelength greater than 1.5 μm. The method includes guiding a mid-infrared beam into the ring resonator.

In yet another example, a method of making a chalcogenide glass ring resonator includes forming a ring ridge comprising chalcogenide glass on a chalcogenide glass substrate. A conformal protective layer is disposed on the ring ridge so as to form a coated ring ridge adjacent to an exposed portion of the chalcogenide glass substrate. The exposed portion of the chalcogenide glass substrate is etched so as to create a chalcogenide glass pedestal extending from the chalcogenide glass substrate and supporting the coated ring ridge. The conformal protective layer is then removed from the coated ring ridge so as to form the chalcogenide glass ring resonator.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 2A-2C show top views of devices including multiple pedestal ring resonators.

FIGS. 3A-3F illustrate a method of fabricating a pedestal ring resonator.

FIGS. 4A-4C illustrate cross sections of different chalcogenide glass resonators including a pedestal ring resonator.

DETAILED DESCRIPTION

Pedestal Ring Resonators

Conventional ring resonators are based mainly on silicon-on-insulator (SOI) technology, in which a layer of silicon dioxide serves as an under-cladding between the top crystalline silicon waveguide and the bottom crystalline silicon substrate to prevent light leakage through the substrate. Though SOI is mature and suitable for near infrared photonic circuits, it cannot be easily adopted for mid-infrared (mid-IR; e.g., $\lambda=3$ μm or longer) devices because silicon dioxide becomes lossy (i.e., absorptive) at wavelengths greater than about 3.6 μm. Due to the multiple passes of light circulating in ring resonators, even a small percentage of loss in one round trip can result in significant decrease of light intensity when the number of round trips adds up.

In addition, when used as sensors, conventional ring resonators generally confine the majority of the light field in the core of the waveguide. The overlap between the evanescent light field and analytes can be weak, thereby limiting the sensing sensitivity.

In view of the challenges in conventional ring resonators, systems, methods, and apparatus described herein include air-clad semiconductor ring resonators. Each of these ring resonators utilizes a pedestal structure supporting the resonator for mid-infrared (mid-IR) devices. The ring resonators are made of silicon or chalcogenide glasses (ChG), which are substantially transparent to mid-infrared radiation. The pedestal structure, which can be made of the same material (silicon or ChG) as the ring resonators, has a narrower width compared to the ring resonator disposed on the pedestal. Simulation results confirm that the pedestal structures allow improved interaction between the evanescent field and analytes nearby the ring resonators, thereby increasing sensing sensitivity. In addition, fabrication of these ring resonators is compatible with complementary metal-oxide-semiconductor (CMOS) processes and hence is amenable to large scale manufacturing.

Figure 1A:
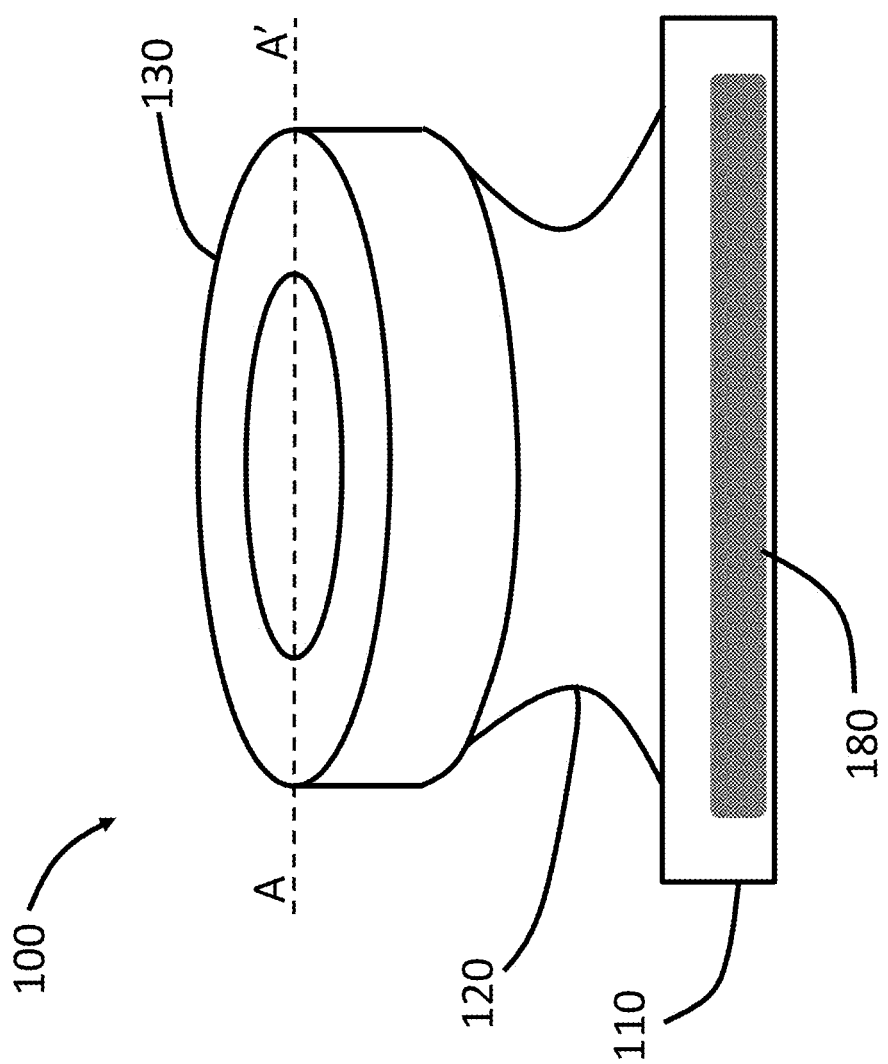
FIGS. 1A-1C show schematics of a pedestal ring resonator.
Figure 1B:
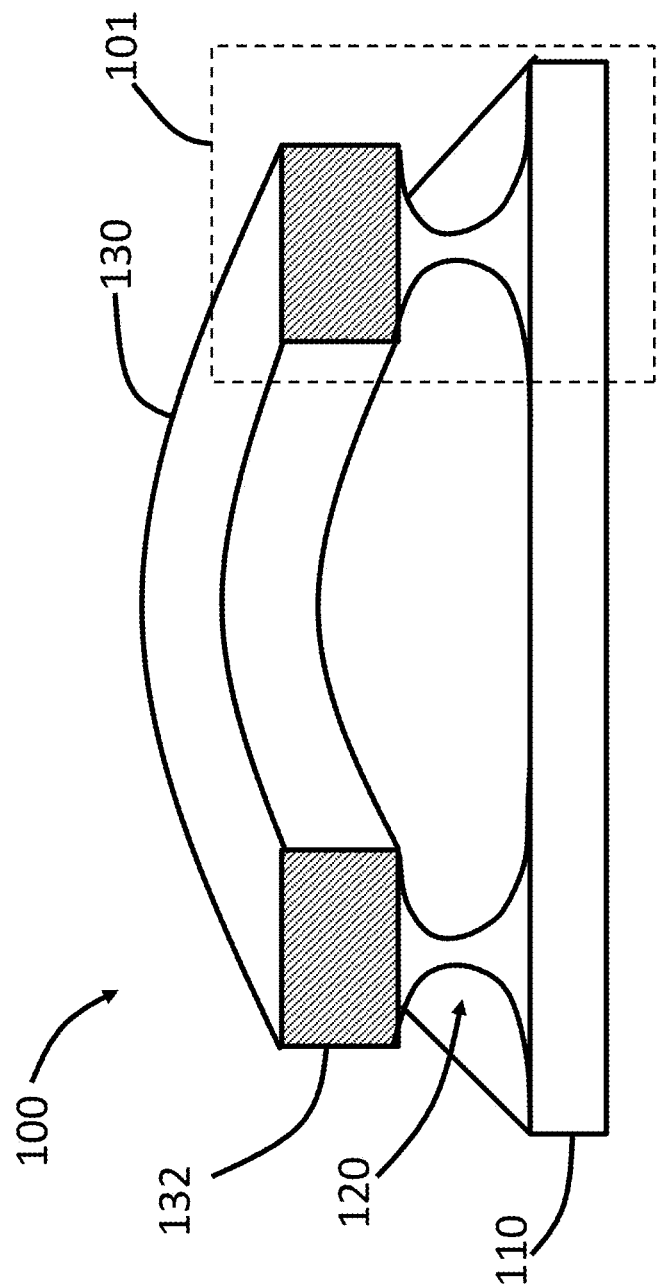
Figure 1C:
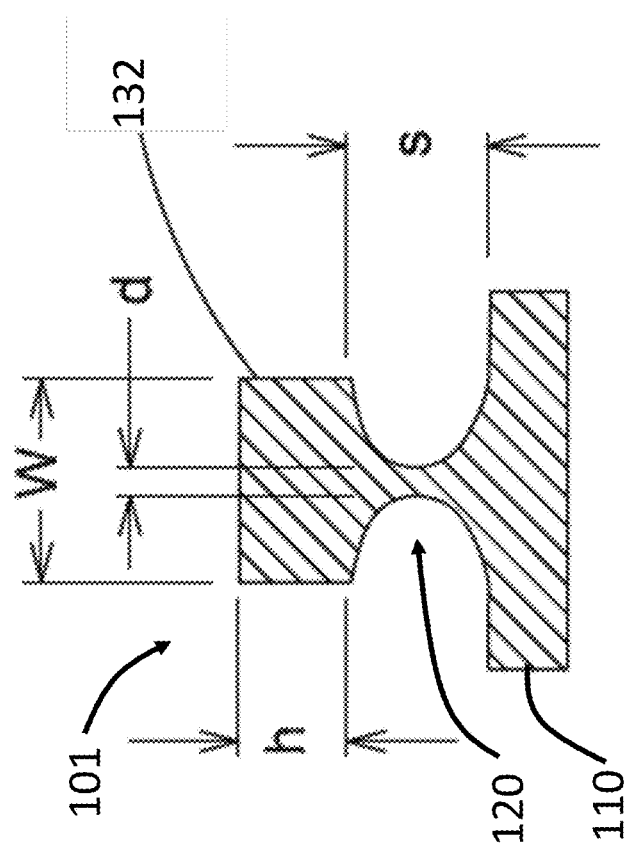

FIGS. 1A-1C show schematics of a semiconductor device including a ring resonator that can allow both low loss for light in the mid-infrared region and strong interaction of evanescent fields with analytes. FIG. 1A shows a perspective view of the device 100. FIG. 1B shows the cross section of the device 100 along the AA' line shown in FIG. 1A. FIG. 1C shows a cross section view 101 (illustrated as the dashed rectangular box in FIG. 1B) of the device 100 with illustrations of dimensions.

The device 100 includes a substrate 110, a pedestal 120 extending from the substrate 110, and a ring resonator 130 disposed on the pedestal 120. The substrate 110 and the pedestal 120 generally include silicon in CMOS processes. In some examples, the substrate 110 and the pedestal 120 can include other materials such as Sapphire, or $CaF_2$. The ring resonator 130 is made of silicon or chalcogenide. As readily known in the art, silicon can be transparent in the near infrared and mid-infrared region (e.g., about 1.1 µm to about 10 µm) and chalcogenide glass can be transparent for even longer wavelengths (e.g., up to 40 µm). Therefore, using silicon or chalcogenide glass in the ring resonator 130 can reduce optical losses when mid-infrared light is circulating in the resonator. As can be seen from the cross section of the device 100 shown in FIG. 1B and FIG. 1C, the ring resonator 130 is wider than the pedestal 120 (put differently, the ring resonator 130 overhangs the pedestal 120), allowing stronger interaction between the evanescent field and analytes nearby the ring resonator 130, in particular near the resonator-pedestal interfaces and resonator edges.

Various types of silicon can be used for the ring resonator 130. In some examples, the ring resonator 130 includes single crystalline silicon (also referred to as sc-Si). In some examples, the ring resonator 130 includes multicrystalline silicon (also referred to as mc-Si). In some examples, the ring resonator 130 includes polycrystalline silicon (also referred to as pc-Si). In some examples, the ring resonator 130 includes amorphous silicon.

Chalcogenide glasses are generally based on chalcogen elements such as sulphur, selenium, tellurium, and polonium. These glasses can be formed by the addition of some other elements such as germanium, arsenic, antimony, or gallium. Various types of chalcogenide glasses can be used for the ring resonator 130. In some examples, the ring resonator 130 includes pure chalcogenide (e.g., S, Se, Te, $S_xSe_{1-x}$). In some examples, the ring resonator 130 includes pnictogen-chalcogen such as (V-VI) $As_2S_3$ or $P_2Se$. In some examples, the ring resonator 130 includes tetragen-chalcogen such as (IV-VI) $SiSe_2$, $GeS_2$ III-VI B2S3, or $In_xSe_{1-x}$. In some examples, the ring resonator 130 includes metal chalcogenide such as $MoS_3$, $WS_3$, or $Ag_2S$—$GeS_2$. In some examples, the ring resonator 130 includes halogen-chalcogenide such as As—Se—I, Ge—S—Br, or Te—Cl.

The ring resonator 130 shown in FIG. 1A has a circular shape and various diameters can be used. In general, the diameter of the ring resonator 130 may depend on, for example, the desired resonance wavelength and/or the desired number of supported longitudinal modes. As understood in the art, the resonance wavelength λ of the mth mode in a ring resonator is $\lambda = D\pi n_{eff}/m$, where D is the resonator diameter, $n_{eff}$ is the effective refractive index (RI) of the mth mode of the ring resonator, and m is an integer. The resonance wavelength of the ring resonator 130 can be about 1 µm to about 40 µm (e.g., 1 µm, 5 µm, 10 µm, 15 µm, 20 µm, 25 µm, 30 µm, 35 µm or 40 µm). In some examples, the ring resonator 130 can support only one longitudinal mode (e.g., m<1 for a given D and λ). In other examples, the ring resonator 130 can support multiple longitudinal modes. In practice, the diameter D of the ring resonator 130 can be about 50 µm to about 150 µm (e.g., 50 µm, 60 µm, 70 µm, 80 µm, 90 µm, 100 µm, 110 µm, 120 µm, 130 µm, 140 µm, or 150 µm).

The resonance wavelength of the ring resonator 130 can also be adjusted by tuning the effective refractive index $n_{eff}$ of the ring resonator 130 by a modulator 180. In some examples, the modulator 180 may include a piezo-electric element or other suitable element configured to apply a mechanical force to the ring resonator 130 so as to modulate the refractive index of the ring resonator 130. The mechanical force can be applied via, for example, compression, bending, stretching, shearing, or any other means known in the art.

In some examples, the modulator 180 is configured to apply an electric field to the ring resonator 130 so as to modulate the refractive index of the ring resonator 130. For instance, the modulator 180 may apply the electric field via two electrodes, with one electrode attached to the top of the ring resonator 130 and the other electrode attached to the bottom of the substrate 110. Alternatively or additionally, the electrodes can be attached to a perimeter of the ring resonator 130.

In some examples, the modulator 180 is configured to vary a temperature of the ring resonator 130 so as to modulate the refractive index of the ring resonator 130. For example, the modulator can include a semiconductor heater fabricated in thermal communication with (e.g., beside) the ring resonator 130 on the substrate 110. In another example, the modulator can include a semiconductor heater fabricated beneath the ring resonator 130 in the substrate 110 (e.g., see FIG. 1A). In yet another example, the modulator can include an external heater such as an oven that substantially encloses the entire device 100 so as to uniformly change the temperature of the ring resonator 130.

In some examples, the modulator 180 is configured to apply an acoustic field to the ring resonator 130 so as to modulate the refractive index of the ring resonator 130. In other examples, the modulator is configured to apply a magnetic field to the ring resonator 130 so as to modulate the refractive index of the ring resonator 130.

If the ring resonator 130 comprises chalcogenide glass, the modulator can apply an optical field on the ring resonator 130 so as to modulate the refractive index of the ring resonator 130. As understood in the art, chalcogenide glasses can exhibit several photo-induced effects, including photo-crystallization, photo-polymerization, photo-decomposition, photo-contraction, photo-vaporization, photo-dissolution of metals, and light-induced changes in local atomic configuration. These changes are generally accompanied by changes in the optical band gap and therefore optical constants. In addition, chalcogenide glasses also have strong third order nonlinear effects. Therefore, the modulator can adjust the optical properties of the ring resonator 130 comprising chalcogenide glasses by applying a modulating optical field (separate from the light circulating in the ring resonator 130) on the ring resonator 130.

Other than circular resonator, some other configurations can also be used for the ring resonator 130. In some examples, the resonator 130 may have an elliptical shape. In some examples, the resonator 130 may have a rectangular shape including four linear waveguides, each of which constitutes one side of the rectangle. Adjacent linear waveguides can be coupled by a 45° reflector. In some examples, the resonator 130 may have a cavity configuration, in which a linear waveguide is enclosed by two reflectors with one reflector on each end of the linear waveguide.

FIG. 1B shows the cross section of the device 100 along the AA' line in FIG. 1A. FIG. 1C shows the cross section 101 indicated as rectangular box in FIG. 1B. FIGS. 1B and 1C show that the ring resonator 130 has a rectangular cross section 132. In practice, various other shapes can be used for the ring resonator 130, including but are not limited to circles, triangles, squares, trapezoids, pentagons, hexagon, octagons, or any other shape known in the art.

In some examples, the cross section 132 of the ring resonator 130 can be chosen to support propagation of only a single transverse mode (e.g., the $TEM_{00}$ mode) of a beam so as to, for example, maintain the intensity profile of the beam. In some examples, the cross section 132 of the ring resonator 130 can be chosen to support propagation of multiple transverse modes so as to, for example, modulate the intensity profile or phase of the beam. The selection of single-mode or multimode operation of the ring resonator 130 can be achieved by adjusting the shape and dimensions of the cross section 132.

In some examples, the ring resonator 130 can further include stress members and/or have a shape or composition selected to preserve the polarization state of the beam propagating through the ring resonator 130. In other words, the ring resonator 130 may be a polarization-maintaining waveguide as readily understood by those of skill in the art.

Since light usually circulates multiple times within the ring resonators before it is coupled out, the surface roughness of the ring resonator 130 can significantly influence the propagating light. In some examples, an outer surface of the ring resonator 130 has a surface roughness smaller than the resonance wavelength, half of the resonance wavelength, a quarter of the resonance wavelength, etc.

With reference to FIG. 1C, various dimensions can be used for the ring resonator 130. For example, the cross section 132 of the ring resonator 130 can have a rectangular cross section with a width W and a height h. Depending on the example, the width W can be about 1 µm to about 30 µm (e.g., 2.5 µm, 5.0 µm, 7.5 µm, 10.0 µm, 12.5 µm, 15.0 µm, 17.5 µm, 20.0 µm, 22.5 µm, 25.0 µm, or 27.5 µm) and the height h can be about 1 µm to about 30 µm (e.g., 2.5 µm, 5.0 µm, 7.5 µm, 10.0 µm, 12.5 µm, 15.0 µm, 17.5 µm, 20.0 µm, 22.5 µm, 25.0 µm, or 27.5 µm).

The shape and dimensions of the cross section 132 of the ring resonator 130 shape can also be chosen to support an evanescent wave (tail) that extends laterally out of the ring resonator 130. As understood by those of skill in the art, an evanescent wave is a near-field wave whose intensity decays exponentially decay as a function of the distance from the boundary at which the evanescent wave is formed—in this case, the outer surface of the ring resonator 130. In operation, at least a portion of the evanescent wave may interact with one or more molecules within a length about equal to the evanescent wave's decay constant. For example, the molecule(s) may absorb one or more of the evanescent wave's spectral components, leading to a spectrally selective reduction in intensity of the wave propagating through the ring resonator 130. Detecting this spectrally selective reduction in intensity (e.g., by measuring the absorption spectrum) can yield an indication of the type and concentration of molecules in the environment (e.g., air, gas, fluid, or polymer) surrounding the ring resonator 130.

FIGS. 1B and 1C also show that the pedestal 120 has curved side surfaces. In practice, various other shapes can be used for the pedestal 120. In some examples, the pedestal 120 has a rectangular cross section with a width narrower than that of the ring resonator 130. In some examples, pedestal 120 can have a trapezoidal cross section or a ridge structure with one end (e.g., the narrower end) supporting the ring resonator 130 and the other end (e.g., the wider end) connecting to the substrate 110. In some examples, the pedestal 120 can have a half-dome cross section with the curved end supporting the ring resonator 130 and the flat end coupled to the substrate.

With reference to FIG. 1C, the pedestal 120 has a width d and a height s. These dimensions may be selected for ease of fabrication and/or to provide the desired performance. For instance, the pedestal width d may be about 0.5 µm to about 2.5 µm (e.g., 0.75 µm, 1.0 µm, 1.25 µm, 1.5 µm, 1.75 µm, 2.0 µm, or 2.25 µm), and the pedestal height s may be about 1.0 µm to about 20 µm (e.g., 2.5 µm, 5.0 µm, 7.5 µm, 10.0 µm, 12.5 µm, 15.0 µm, or 17.5 µm). The pedestal 120 may be smoothly tapered at its top and/or its bottom to provide increased stability and/or to reduce mechanical stress and strain on the device 100 and its components.

Figure 2D:
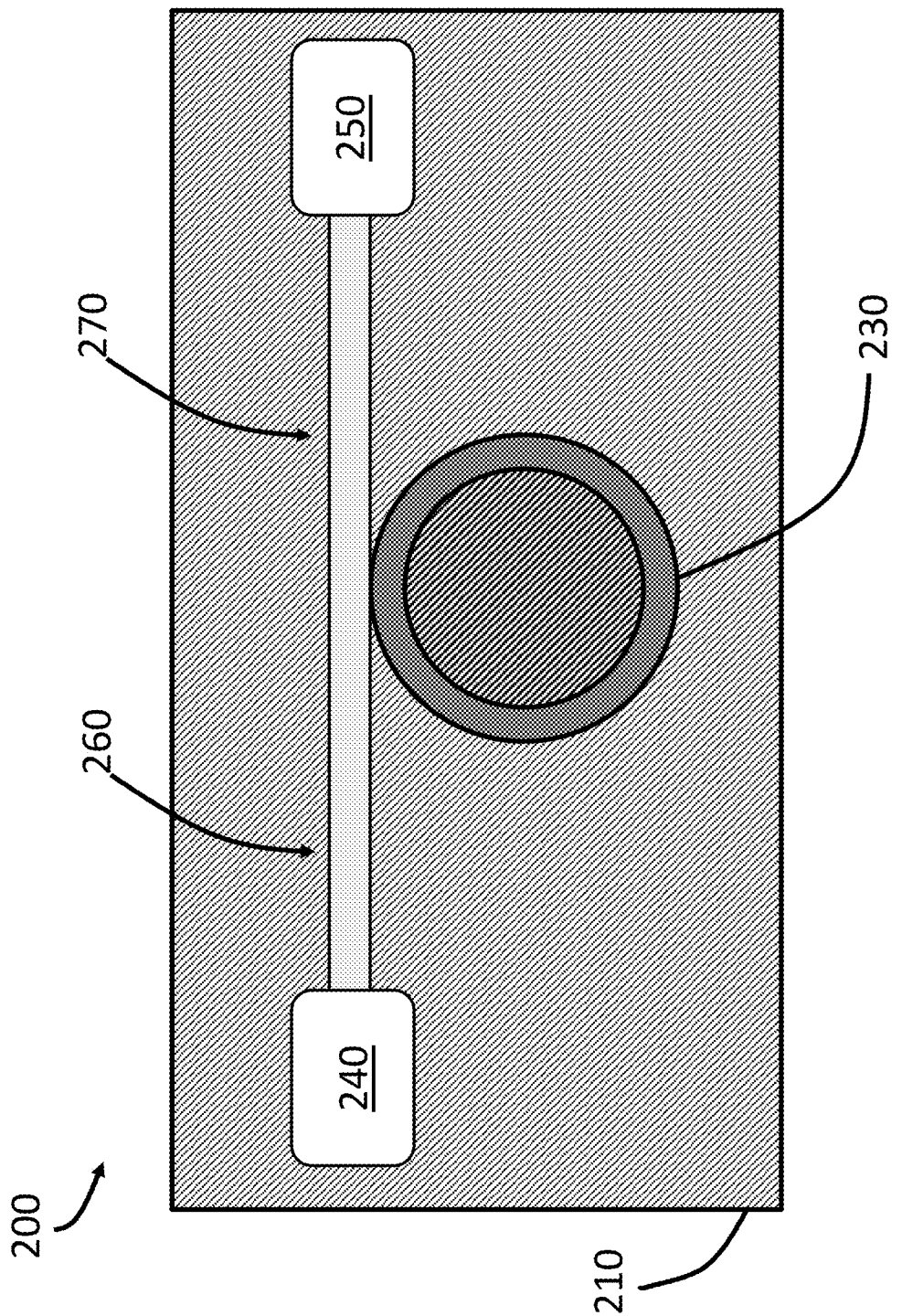
FIG. 2D shows a top view of a sensor including pedestal ring resonators.

FIGS. 2A-2C show top views of devices that include multiple ring resonators, each of which can have a different resonance wavelength. The ring resonators shown in FIGS. 2A-2C can be supported by pedestals (not seen in top views) substantially like the pedestal 120 shown in FIGS. 1A-1C and those described in detail above.

FIG. 2A shows a device 201 including a substrate 211 on which a first ring resonator 231a and a second ring resonator 231b are disposed. The first ring resonator 231a has a larger diameter than the second ring resonator 231b and the second ring resonator 231b is disposed within the cavity (or space) 221 defined by the first ring resonator 231a. This configuration may save space and therefore allow compact design of devices when multiple resonators are used.

FIG. 2B shows a device 202 including a substrate 212 on which a first ring resonator 232a and a second ring resonator 232b are disposed. The first ring resonator 232a has a larger diameter than the second ring resonator 232b. In FIG. 2B, the second ring resonator 232b is disposed within the cavity defined by the first ring resonator 232a and the two ring resonators 232a and 232b are substantially concentric. This configuration may allow uniform or synchronous tuning of the resonance wavelengths of the two ring resonators 231a and 232b via, for example, a heater disposed beneath the ring resonators 232a and 232b in the substrate 212.

FIG. 2C shows a device 203 including a substrate 213 on which a first ring resonator 233a and a second ring resonator 233b are disposed. The two ring resonators 233a and 233b are disposed side by side, which can be beneficial when independent control of each ring resonator is desired.

Other than diameter, different ring resonators in the devices 201 to 203 can also have other different properties, including different cross sectional dimensions, material, and modulation methods for resonance wavelength tuning.

FIGS. 2A-2C each show two ring resonators on one substrate. In practice, more than two ring resonators can be fabricated on the same substrate. These ring resonators can be arranged in various configurations. In some examples, multiple ring resonators can be arranged in arrays, including one-dimensional (1D) arrays, two-dimensional (2D) arrays, and three-dimensional (3D) arrays (e.g., one layer of 2D array of ring resonators is disposed on another layer of 2D ring resonators). In some examples, multiple ring resonators can be in substantially concentric configurations. In some examples, two or more ring resonators can be fabricated side by side but within a cavity defined by a larger ring resonator.

Sensors Including Pedestal Ring Resonators

The pedestal ring resonators described in relation to FIGS. 1A-2C and FIGS. 2A-2C can be used in sensors to sense analytes. FIG. 2D shows a sensor 200 including a ring resonator 230 disposed on a substrate 210. The sensor 200 also includes a light source 240 to provide the light circulating in the ring resonators 230 and a detector 250 to detect optical properties of the light so as to identify the presence or absence of the analytes. An input coupler 260 is used to couple the light into the ring resonator 230 and an output coupler 270 is used to couple the light out of the ring resonator 230. In practice, it can be beneficial to fabricate the pedestal ring resonator(s), the light source, and the detector on the same substrate so as to yield a compact on-chip sensor.

The light source 240 may include one or more narrowband/coherent emitters (e.g., quantum cascade lasers), broadband emitters, or tunable emitters to emit a beam of mid-IR light. For example, the light source may emit a beam at a wavelength that can span or be tuned over some or all of the mid-IR portion of the electromagnetic spectrum, e.g., over a bandwidth of about 1.0 µm to about 40 µm (e.g., about 2 µm, 5 µm, 10 µm, 15 µm, 20 µm, 25 µm, 30 µm, 35 µm, or 40 µm).

In some examples, the wavelength of the light emitted by the light source 240 can be tuned or chosen based on known characteristic absorption bands to monitor a fluid for one or more particular chemicals. For example, hexane has a distinguishable absorbance at $\lambda=3.55$ µm, so tuning the probe light to this wavelength yields a signal that can be used to detect hexane relatively easily. Likewise, to detect a compound that includes an amine functional group, the probe beam's wavelength may be between $\lambda=2.85$ µm and $\lambda=3.22$ µm to interrogate absorption from the N—H stretch associated with the amine functional group. A sensor with multiple ring resonators, such as one resonating at 3.55 µm, another resonating at 2.85 µm, and a third resonating at 3.22 µm can simultaneously monitor hexane and compounds including an amine functional group. Such a sensor may use a broadband source that emits light with spectral components at 3.55 µm, 2.85 µm, and 3.22 µm.

The input coupler 260 is used to couple the light from the light source 240 to the ring resonator(s) 230 in the sensor 200. In some examples, the input coupler 260 includes waveguides evanescently coupled to the ring resonator(s). In some examples, input the coupler 260 includes directional couplers which can control the ratio of light that is transmitted from the light source to the ring resonator(s).

The detector 250 can be optically coupled to the ring resonator(s) using similar output couplers 270 as the input coupler 260 for the input beam and can monitor the output beam from the ring resonator(s) 230. The detector 250 can include one or more broadband sensing elements and/or spectrally selective narrowband sensing elements. For example, the detector 250 can include a spectrometer formed by a grating or other dispersive element that directs different spectral components of a broadband beam into different angles, each of which is monitored by a respective detector element in a detector array (e.g., a charged coupled device (CCD) or complementary metal-oxide-semiconductor (CMOS) sensing array) to yield the absorption spectrum of the absorbers evanescently coupled to the sensor. Alternatively or additionally, the detector 250 may include a single sensing element that detects the time-varying intensity of a spectrally swept (chirped) beam. Mapping the resulting time-varying intensity signal to the spectral sweep speed yields an absorption spectrum that can be used to identify any absorbers evanescently coupled to the sensor.

In operation, the sensor 200 can be exposed to a fluid (e.g., gas or liquid) to be analyzed for the presence (or absence) of one or more particular chemicals or compounds. For instance, the fluid may be a liquid that is dropped onto the sensor with a pipette. The sensor 200 may also be immersed in fluid or placed in a fluid flow. If desired, the sensor 200 may be integrated with one or more micro-fluidic devices to prevent evaporation and improve device stability.

At least some of the fluid extends over or near at least a portion of the sensor's ring resonator(s) 230. As light from the light source 240 circulates within the ring resonator(s) 230, the fluid may alter the properties of the light or alter the properties of the ring resonators 230. By monitoring the properties of the light or the ring resonators 230, the presence (or the absence) of the analytes can be determined.

Depending on the properties monitored by the detector, several types of sensing can be carried out by sensors including the pedestal ring resonators.

The sensor 200 can be configured to perform refractive index (RI) sensing. When analytes are present in the evanescent field of the resonant mode, the refractive index experienced by the resonant modes in the ring resonators can change, because analytes usually have RIs different from that of the surrounding medium. This RI change can lead to a spectral shift in the resonant mode, which can be detected directly or indirectly (through intensity or phase detection) as indication of the presence of analytes.

The sensor can be configured to perform fluorescence sensing. In general, photons in the ring resonator can excite the analytes so as to induce fluorescence. The analytes can be a natural chromophore, which can emit fluorescence light once excited. Or the analytes may not emit fluorescence directly but can be labeled with fluorophores such as dyes. The signal from the fluorescence can be proportional to the Q-factor of the resonator(s) in the sensor. For a sensor with ring resonators that have a high Q-factor, nonlinear excitation (e.g., two-photon or multi-photon excitation) can be used to excite biochemical samples whose absorption band is in the ultraviolet (UV) region of the electromagnetic spectrum.

The sensor can also be configured to perform absorption sensing. Absorption measurements can be carried out by tuning the resonant wavelength across the absorption band of the analytes for enhanced absorption path length. In some examples, when the Q-factor of the ring resonator(s) is high (e.g., $>10^6$, $>10^7$, or $>10^8$), absorption sensing can be carried out by monitoring the degradation of the resonant mode Q-factor. The degradation of the Q-factor can be caused by the extra loss induced by optical absorption.

The sensor can be configured to perform Raman sensing. Raman spectroscopy in general relies on inelastic scattering, or Raman scattering, of monochromatic light photons with molecules. The light interacts with molecular vibrations, phonons, or other excitations in the system, resulting in up-shift or down-shift of the light photon energy. The energy shift can be characteristic to certain molecules and therefore can help identify the presence of these molecules. Measurements by the ring resonator(s) in the sensor can also be combined with Raman spectroscopy to increase the Raman signals, which can lead to a gain over two orders of magnitude. Using a high-Q ring resonator can also induce stimulated Raman emission, which can be employed for identification of species in liquid.

The sensor can perform surface sensing, bulk sensing, or both. Surface sensing signals come from analytes in close proximity to the ring resonator surface (much closer than the evanescent field decay length) whereas bulk sensing signals result from the optical change induced by the presence of the analytes in the whole region of the evanescent field.

Light Sources Including Pedestal Ring Resonators

The ring resonators described in relation to FIGS. 1A-2C and FIGS. 2A-2C can also be used in light sources. In some examples, the ring resonators can be optically coupled to the output of a broadband light source so as to deliver light at a particular wavelength. Generally, only light at a wavelength at or near the resonance wavelength of the ring resonator can circulate in the ring resonator. Therefore, a ring resonator coupled to the output of a broadband light source can deliver narrowband light at the resonance wavelength of the ring resonator. Since ring resonators described herein are substantially transparent in the mid-infrared region, they can be helpful in constructing narrowband, mid-infrared light sources.

Multiple ring resonators (e.g., the devices shown in FIGS. 2A-2C) can be coupled to the output of a broadband light source so as to deliver narrowband beams at different wavelengths from a single broadband light source. Modulators can be used to tune the resonance wavelength of the ring resonators so as to tune the output wavelength of the light beams. Since ring resonators used as wavelength selectors are generally passive, tuning the properties of the ring resonators (e.g., temperature) can have less effect on the beam quality than tuning the light source.

In some examples, the ring resonators can be doped with active materials (lasing materials) so as to function as a laser cavity and therefore as a light source. For example, chalcogenide ring resonators may be doped with rare earth elements, such as Er, Nd, Pr, or any other element known in the art, to function as laser cavities or optical amplifiers.

Sensors and light sources are described here for illustrating and non-limiting purposes only. In practice, ring resonators described herein can be used in various other applications such as optical/infrared delay lines, spectral filters and switches, directional couplers, or any other application known in the art.

Methods of Fabricating Pedestal Ring Resonators

FIGS. 3A-3F illustrate a method 300 of fabricating pedestal ring resonators. In the method 300, pedestal ring resonators made of chalcogenide glasses (ChG) are fabricated. In practice, this method can be extended to other materials such as silicon.

FIG. 3A shows a ChG multi-layer structure 330 (also referred to as a ChG layer 330), on which a sacrificial layer 320 is disposed. A photo resist layer 310 is disposed on the sacrificial layer 320. Photolithography can be used to transfer the pattern on the photo resist layer 310 to both the sacrificial layer 320 and the ChG layer 330. The etching can partially remove the ChG layer 330 but not into the underlying $CaF_2$ film (not shown) so as to protect the $CaF_2$ film. The etching can also hollow out a large part of the region beneath the edges of the ChG layer 330, allowing mode expansion for greater photon-analyte interaction in sensing.

The sacrificial layer 320 can be silicon nitride prepared by room temperature sputtering deposition. In some examples, the sacrificial layer 320 can be silicon nitride prepared by low temperature (e.g., <150° C.) plasma-enhanced chemical vapor deposition (PECVD). For a sputtering process, the deposition rate can be 30-50 angstroms per minute and the deposition time can be two hours to reach a film thickness of 360-600 nm. In some examples, for PECVD silicon nitride, the reactive gases (or etching gas) can be $SiH_4$, $NH_3$, and $N_2$ and the deposition rate can be 150 angstroms per minute. A total deposition time can be 30 minutes to prepare a 450 nm sacrificial layer.

FIG. 3B shows that a ring ridge 335 (only the cross section is shown) is formed in the ChG layer 330. The sacrificial layer 320 is also etched together with the ChG layer 330, and the leftover part of the sacrificial layer 320 covers the ring ridge 335.

FIG. 3C shows that a protective layer 340 (also referred to as protective coating) is disposed on the sides of the ring ridge 335, the sacrificial layer 320, and the exposed portion of the ChG layer 330. The protective layer 340 can be conformally deposited on the sample to cover all exposed surfaces, including the side surfaces of the ring ridge 335. The protective layer 340 may include a polymer such as Poly(methyl methacrylate) (PMMA) or Poly(Glycidyl Methacrylate) (PGMA). In some examples, the polymer can be deposited using spin coating. In some examples, the protective layer 340 includes silicon nitride deposited by PECVD processes.

FIG. 3D shows that the protective layer 340 is selectively removed. More specifically, the protective layer 340 is etched on top surfaces, including the portion on the top surface of the sacrificial layer 320 and the portion on the exposed surfaces of the ChG layer 330. The PMMA protective layer can be removed using, for example, Acetone or oxygen plasma etching. The silicon nitride protective layer can be removed using for example, dry etching or wet etching. In one example, the silicon nitride protective layer can be left on the device without removal (i.e. the method can function without step shown in FIG. 3D).

FIG. 3E shows that part of the remaining ChG layer 330 is undercut to form a pedestal 338 supporting the ring ridge 335, the sacrificial layer 320, and the remaining protective layer 340 on side surfaces of the ring ridge 335. The undercut can be performed by isotropic etching using liquid ethylenediamine at room temperature.

FIG. 3F shows a pedestal ring resonator including a ChG layer 330, a pedestal 338, and a waveguide 335 (the ring ridge 335) supported by the pedestal 338. At this step, the remaining protective layer 320 on the side surfaces of the ring ridge 335 is removed, e.g., using one or more solvents, such as acetone.

Characterization of Pedestal Ring Resonators

FIGS. 4A-4C illustrate cross sections of three configurations of ring resonators that can be used for sensing. More specifically, FIG. 4A shows the refractive index profile of a rectangular ring resonator 401 including a single-mode rectangular waveguide core 421. FIG. 4B shows the refractive index profile of a pedestal ring resonator 402 including a single-mode waveguide core 422 disposed on a pedestal 432. FIG. 4C shows the refractive index profile of a narrow ring resonator 403 including a narrow waveguide (narrower than single-mode waveguide) 433. The resonators 421, 422, and 423, as well as the pedestal 432, are made of chalcogenide glass having a high refractive index of 2.4. A $CaF_2$ under-cladding 410 having a refractive index of 1.4 is used for all resonators. In addition, the resonators are disposed in the same surrounding chemical 430.

Figures 5A, 5B, 5C:
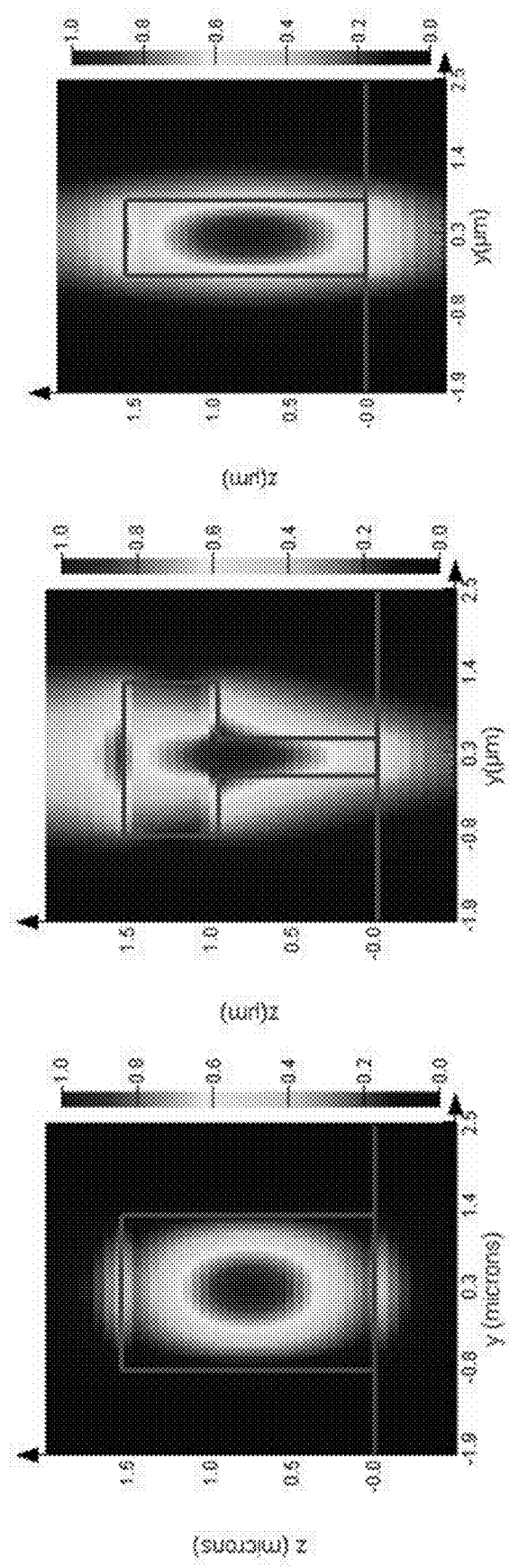
FIGS. 5A-5C illustrate the optical fields of light circulating in the resonators shown in FIGS. 4A-4C.

FIGS. 5A-5C show calculated mode profiles of the three configurations of ring resonators shown in FIGS. 4A-4C, respectively. FIG. 5A shows the mode profiles in the ring resonator having a rectangular waveguide as shown in FIG. 4A. The rectangular ring resonator confines the majority of the light within the waveguide boundaries (shown as solid lines in the intensity distribution) and very little evanescent field exists.

FIG. 5B shows mode profiles of the pedestal ring resonator illustrated in FIG. 4B. A strong evanescent field overlaps with the external analytes, in particular at the interface between the waveguide and the pedestal as well as on the top surface of the waveguide. This strong evanescent field can improve sensitivity when the ring resonator is used as a sensor.

FIG. 5C shows mode profiles of the narrow pedestal ring resonator illustrated in FIG. 4C. The light within the narrow waveguide can also enhances light-analyte interaction, but this interaction is limited to the top surface of the waveguide and is not as strong as in the pedestal structure seen in FIG. 5B.

From these calculations, the pedestal structure (FIG. 5B), compared to the rectangular configuration (FIG. 5A) can achieve an improvement in sensitivity by a factor of 2.91, at least because of enhanced light matter interaction occurring around the waveguide interfaces and edges. The narrow waveguide configuration (FIG. 5C) can also achieve some improvement (~1.77 times enhancement), but less that achieved by the pedestal structure.

Figure 6B:
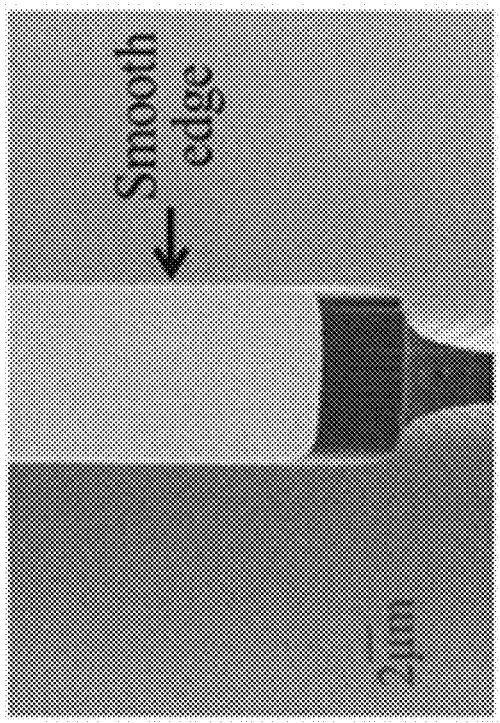
FIGS. 6A and 6B are scanning electron microscopy (SEM) images of pedestal waveguides with smooth edges.
Figure 6A:
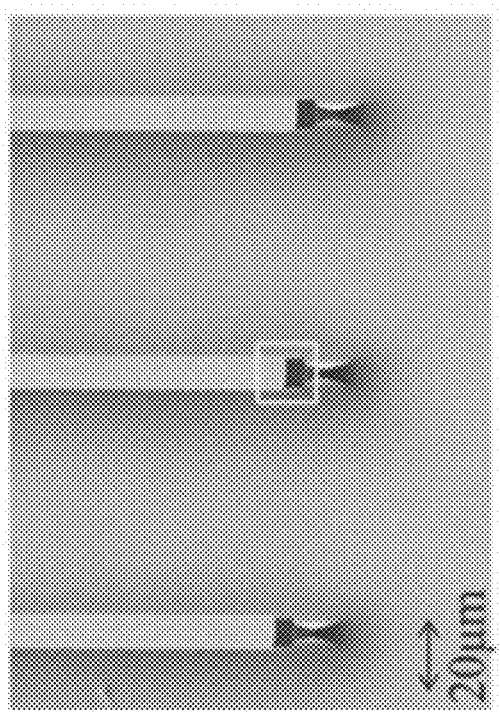

FIGS. 6A-6B show scanning electron microscopy (SEM) images of pedestal waveguides (silicon-on-insulator). These waveguides are linear waveguides. Fabricating pedestal microring and microdisk resonators can be achieved by using appropriately dilute wet etch solutions with carefully monitored temperature and time in the etching bath.

The samples shown in FIGS. 6A-6B are tilted at 54° during microscopy to improve the cross sectional images. From FIG. 6A and its magnified image FIG. 6B, it can be readily seen that the waveguide edges (top of the structure) are smooth without bumps or indentations. In addition, the waveguide edges remain straight without bending or distortion. The waveguide structure is also well-resolved. No cracks or roughness is seen on the waveguide edges. From the magnified image the structure parameters (designations can be found in FIG. 1C) are W=8 µm, h=5 µm, s=14 µm, and d=2 µm. Furthermore, no defects are found in the vertical facets, confirming that the conformally deposited protective layer can effectively protect the waveguide during etching.

Conclusion

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the technology disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:
1. A device comprising:
   a substrate;
   a pedestal extending from the substrate; and a ring resonator disposed on the pedestal above the substrate and having a resonance wavelength greater than 1.5 µm,
wherein the ring resonator comprises at least one of silicon and chalcogenide glass.

2. The device of claim 1, wherein a first width of the pedestal is smaller than a second width of the waveguide.

3. The device of claim 1, wherein the pedestal has a minimum width of about 0.5 µm to about 2.5 µm and a height of about 1.0 µm to about 20 µm.

4. The device of claim 1, wherein the ring resonator has a cross section with a width of about 1 µm to about 20 µm and a height of about 0.4 µm to about 20 µm.

5. The device of claim 1, wherein the ring resonator has an outer diameter of about 50 µm to about 150 µm.

6. The device of claim 1, wherein the ring resonator comprises a single mode waveguide at the resonance wavelength.

7. The device of claim 1, wherein the ring resonator comprises silicon and the resonance wavelength is within a range of about 1.5 µm to about 6 µm.

8. The device of claim 1, wherein the ring resonator comprises chalcogenide glass and the resonance wavelength is greater than about 6 µm.

9. The device of claim 1, wherein the ring resonator defines an outer surface to receive at least one molecule so as to cause absorption of light propagating in the ring resonator and detect the at least one molecule.

10. The device of claim 1, wherein the ring resonator defines an outer surface having a surface roughness smaller than a quarter of the resonance wavelength.

11. The device of claim 1, further comprising:
a modulator, operably coupled to the ring resonator, to modulate the resonance wavelength of the ring resonator.

12. The device of claim 11, wherein the modulator is configured to modulate the resonance wavelength by applying at least one of a mechanical force, an electric field, a magnetic field, an acoustic field, or a thermal field to the ring resonator.

13. The device of claim 1, further comprising:
an input coupler, evanescently coupled to the ring resonator, to couple light at the resonance wavelength into the ring resonator; and
an output coupler, evanescently coupled to the ring resonator, to couple at least a portion of the light at the resonance wavelength out of the ring resonator.

14. The device of claim 13, further comprising:
a mid-infrared light source, optically coupled to the input coupler, to launch the light at the resonance wavelength into the ring resonator via the input coupler; and
a detector, optically coupled to the output coupler, to detect the at least a portion of the light at the resonance wavelength transmitted through the ring resonator and the output coupler.

15. The device of claim 1, wherein the ring resonator is a first ring resonator and the resonance wavelength is a first resonance wavelength and further comprising a second ring resonator having a second resonance wavelength different from the first resonance wavelength.

16. The device of claim 15, wherein the second ring resonator is disposed substantially within a cavity defined by the first ring resonator.

17. The device of claim 15, wherein the first ring resonator is substantially concentric with the second ring resonator.

18. A method of detecting a molecule using a device comprising a substrate, a pedestal extending from the substrate, and a ring resonator disposed on the pedestal above the substrate, the ring resonator comprising at least one of silicon and chalcogenide glass and having a resonance wavelength greater than 1.5 µm, the method comprising:
guiding a mid-infrared beam into the ring resonator.

19. The method of claim 18, wherein the ring resonator comprises silicon and the mid-infrared beam has a wavelength of about 1.5 µm to about 6 µm.

20. The method of claim 18, wherein the ring resonator comprises chalcogenide glass and the mid-infrared beam has a wavelength greater than 6 µm.

21. The method of claim 18, further comprising:
modulating the resonance wavelength of the ring resonator by applying at least one of a mechanical force, an electric field, a magnetic field, an acoustic field, or a thermal field on the ring resonator.

22. The method of claim 18, further comprising:
coupling the mid-infrared beam into the ring resonator via an input coupler evanescently coupled to the ring resonator; and
coupling the mid-infrared beam out of the ring resonator via an output coupler evanescently coupled to the ring resonator.

23. The method of claim 18, further comprising:
exposing an outer surface of the ring resonator to at least one molecule; and
detecting the mid-infrared beam propagating in the ring resonator so as to identify the at least one molecule.

24. The method of claim 18, further comprising:
tuning a wavelength of the mid-infrared beam to match the resonance wavelength.

25. The method of claim 18, wherein the ring resonator is a first ring resonator and the resonance wavelength is a first resonance wavelength, wherein guiding the mid-infrared beam further comprises guiding the mid-infrared beam in a second ring resonator having a second resonance wavelength different from the first resonance wavelength.

26. A method of making a chalcogenide glass ring resonator, the method comprising:
A) forming a ring ridge comprising chalcogenide glass on a chalcogenide glass substrate;
B) disposing a conformal protective layer on the ring ridge so as to form a coated ring ridge adjacent to an exposed portion of the chalcogenide glass substrate;
C) etching the exposed portion of the chalcogenide glass substrate so as to create a chalcogenide glass pedestal extending from the chalcogenide glass substrate and supporting the coated ring ridge; and
D) removing the conformal protective layer from the coated ring ridge so as to form the chalcogenide glass ring resonator.

27. The method of claim 26, wherein A) comprises:
A1) depositing a sacrificial layer on the chalcogenide glass substrate;
A2) forming a patterned photoresist layer on the sacrificial layer; and
A3) etching the chalcogenide glass substrate adjacent to the patterned photoresist layer so as to form the ring ridge beneath the patterned photo resist layer using photolithography, and
wherein D) further comprises removing the sacrificial layer.

28. The method of claim 27, wherein A1) comprising depositing a silicon oxide layer on the chalcogenide glass substrate.

29. The method of claim 26, wherein B) comprises depositing at least one of a polymer layer or a silicon nitride layer on the ring ridge.

30. The method of claim 26, wherein C) comprises etching the exposed portion of the chalcogenide glass substrate using ethylenediamine.

* * * * *